United States Patent
Anderson et al.

(10) Patent No.: US 10,039,231 B2
(45) Date of Patent: Aug. 7, 2018

(54) SYSTEM FOR MEASURING PLANT ATTRIBUTES USING A PRIORI PLANT MAPS

(71) Applicant: Deere & Company, Moline, IL (US)

(72) Inventors: Noel W. Anderson, Fargo, ND (US); Niels Dybro, Sherrard, IL (US)

(73) Assignee: Deere & Company, Moline, IL (US)

( * ) Notice: Subject to any disclaimer, the term of this patent is extended or adjusted under 35 U.S.C. 154(b) by 81 days.

(21) Appl. No.: 14/716,136

(22) Filed: May 19, 2015

(65) Prior Publication Data

US 2016/0338267 A1    Nov. 24, 2016

(51) Int. Cl.
| | |
|---|---|
| A01D 45/02 | (2006.01) |
| A01D 41/127 | (2006.01) |
| A01D 75/00 | (2006.01) |
| G01B 21/08 | (2006.01) |
| G01B 21/10 | (2006.01) |
| G01N 3/30 | (2006.01) |
| A01B 79/00 | (2006.01) |

(52) U.S. Cl.
CPC .......... *A01D 45/02* (2013.01); *A01D 41/127* (2013.01); *A01D 45/021* (2013.01); *A01D 75/00* (2013.01); *G01B 21/08* (2013.01); *G01B 21/10* (2013.01); *G01N 3/30* (2013.01); *A01B 79/005* (2013.01)

(58) Field of Classification Search
CPC .................................................... A01D 45/02
See application file for complete search history.

(56) References Cited

U.S. PATENT DOCUMENTS

| | | | | |
|---|---|---|---|---|
| 5,995,895 A | * | 11/1999 | Watt | A01B 79/005 56/10.2 G |
| 6,061,618 A | * | 5/2000 | Hale | G01C 21/20 342/357.52 |
| RE37,574 E | * | 3/2002 | Rawlins | A01B 79/005 702/2 |
| 6,553,312 B2 | * | 4/2003 | Upadhyaya | A01C 21/005 342/357.31 |
| 7,725,233 B2 | * | 5/2010 | Hendrickson | A01B 69/008 701/50 |
| 7,930,085 B2 | * | 4/2011 | Anderson | G06Q 10/00 700/284 |
| 8,010,261 B2 | * | 8/2011 | Brubaker | A01D 41/1278 460/1 |
| 8,150,554 B2 | * | 4/2012 | Anderson | G06Q 50/06 47/1.5 |
| 8,321,365 B2 | * | 11/2012 | Anderson | G06N 5/02 706/46 |

(Continued)

FOREIGN PATENT DOCUMENTS

EP    2764764 A1    8/2014

OTHER PUBLICATIONS

European Search Report in foreign counterpart application No. 16169892.3 dated Oct. 12, 2016 (8 pages).

*Primary Examiner* — Harshad R Patel
*Assistant Examiner* — Tran M Tran
(74) *Attorney, Agent, or Firm* — Rathe Lindenbaum LLP

(57) ABSTRACT

A system for measuring plant attributes comprises a plant attribute sensor (103, 108, 110); a digital a priori plant location map (118); and an ECU (126) coupled to the plant attribute sensor (103, 108, 110) and configured to retrieve and use the a priori plant map and to anticipate a plant measurement based upon the a priori plant map and to use that anticipation to improve the accuracy of the plant measurement.

17 Claims, 2 Drawing Sheets

(56) References Cited

U.S. PATENT DOCUMENTS

| | | | | |
|---|---|---|---|---|
| 8,340,438 B2* | 12/2012 | Anderson | ............ | G05D 1/0088 |
| | | | | 348/E7.086 |
| 8,381,501 B2* | 2/2013 | Koselka | ................ | A01D 46/30 |
| | | | | 56/10.2 A |
| 8,407,157 B2* | 3/2013 | Anderson | ............ | A01B 69/008 |
| | | | | 701/50 |
| 8,818,567 B2* | 8/2014 | Anderson | ............ | G05D 1/0088 |
| | | | | 701/2 |
| 9,232,693 B2* | 1/2016 | Hendrickson | ........ | A01D 45/025 |
| 9,282,693 B2* | 3/2016 | Anderson | ............ | A01B 79/005 |
| 9,310,329 B2* | 4/2016 | Acheson | ............ | G01N 27/223 |
| 9,322,629 B2* | 4/2016 | Sauder | ................ | A01D 45/021 |
| 9,372,109 B2* | 6/2016 | Acheson | ............ | G01G 11/003 |
| 9,410,840 B2* | 8/2016 | Acheson | ............ | G01G 11/003 |
| 9,668,420 B2* | 6/2017 | Anderson | ............ | A01D 75/00 |
| 2006/0150601 A1* | 7/2006 | Britton | .................. | A01D 44/00 |
| | | | | 56/8 |
| 2009/0282794 A1 | 11/2009 | Wilcox et al. | | |
| 2014/0059994 A1* | 3/2014 | Surmann | ............. | A01D 45/021 |
| | | | | 56/60 |
| 2014/0075908 A1* | 3/2014 | Surmann | ............. | A01D 45/021 |
| | | | | 56/119 |
| 2014/0083073 A1* | 3/2014 | Doerscher, Sr. | ....... | A01D 47/00 |
| | | | | 56/56 |
| 2014/0230396 A1* | 8/2014 | Dybro | .................. | A01D 45/021 |
| | | | | 56/62 |
| 2014/0236381 A1* | 8/2014 | Anderson | ............. | A01D 75/00 |
| | | | | 701/1 |
| 2015/0082760 A1* | 3/2015 | Zentner | ................ | A01D 45/021 |
| | | | | 56/62 |
| 2016/0330907 A1* | 11/2016 | Anderson | .......... | A01D 41/1278 |

\* cited by examiner

500
SYSTEM FOR MEASURING PLANT ATTRIBUTES USING A PRIORI PLANT MAPS

RELATED APPLICATIONS

This application is related to U.S. patent application Ser. No. 14/712,449 which was filed May 13, 2015 and is assigned to the owner of the present application. This application is incorporated herein by reference for all that it teaches.

FIELD OF THE INVENTION

The invention relates to electronic systems for measuring plant attributes during harvesting. More particularly, it relates to using electronic plant maps to create a sensor sampling window in which the plant attributes are measured.

BACKGROUND OF THE INVENTION

Systems have been proposed to measure attributes of crop plants during harvesting. In particular, row crop harvesters, such as corn heads mounted on agricultural combines for harvesting corn use plant attribute sensors such as sensors for detecting the diameter or thickness of cornstalks, as well as sensors for measuring the impact of ears of corn when they are stripped from the stalk of the corn plant.

Signals from impact sensors on row crop harvesting heads such as corn heads can be electronically processed to indicate plant attributes such as the number of ears on a corn plant, the mass of each ear, the amount of seed on the ear, and crop yields.

Both impact sensors and crop thickness sensors, however, suffer from noise (i.e. spurious sensor signals) due to extraneous vibrations in the machine as well as trash from the field or from portions of other crop plants.

This noise may be large enough that an electronic control unit (ECU) receiving signals from the plant attribute sensors can erroneously interpret this noise as a plant attribute.

A co-pending application (U.S. patent application Ser. No. 14/712,449) addresses this problem in a system for measuring plant attributes by using a vehicle guidance sensor disposed in front of the plant attribute sensors to sense individual corn plants approaching plant attribute sensors and to establish a sensor sampling window within which signals from the plant attribute sensors are gathered for processing to determine plant attributes, and outside of which signals from the plant attribute sensors are not gathered and processed to determine plant attributes.

One problem with this arrangement is that it requires a vehicle guidance sensor to establish the sensor sampling window.

What is needed is a system that anticipates the presence of plants that does not require the use of vehicle guidance sensors. It is an object of this invention to provide such a system.

SUMMARY OF THE INVENTION

In accordance with one aspect of the invention, a system for measuring plant attributes during harvesting of a row crop is provided, comprising: a plant attribute sensor (103, 108, 110); a digital a priori plant location map (118); and an ECU (126) coupled to the plant attribute sensor (103, 108, 110) and configured to retrieve and use the a priori plant location map (118) to anticipate the presence of a plant to be harvested and to use the anticipated presence of a plant to improve accuracy of a plant measurement, wherein the plant measurement is provided by the plant attribute sensor (103, 108, 110).

The ECU may be configured to create a sensor sampling window (210), wherein the ECU (126) is further configured to receive data from the plant attribute sensor (103, 108, 110) during the sensor sampling window (210) and wherein the ECU (126) is further configured to reject data from the plant attribute sensor (103, 108, 110) outside of the sensor sampling window.

The anticipated plant measurement may be used to adjust a value of as-received data from the plant attribute sensor (103, 108, 110).

The plant attribute sensor may comprise at least one of a feeler-based plant sensor (103), a stripper plate plant sensor (108), and a plant impact sensor (110).

The feeler-based plant sensor (103) may be a vehicle guidance sensor.

The stripper plate plant sensor (108) may be configured to generate a signal indicative of a plant stalk thickness for a crop plant disposed between two stripper plates (104).

The plant impact sensor (110) may be configured to respond to impacts of ears of corn on a stripper plate (104).

The system may further comprise a second plant attribute sensor (103, 108, 110), wherein the second plant attribute sensor (103, 108, 110) is coupled to the ECU (126), and wherein the second plant attribute sensor (103, 108, 110) comprises at least another of the feeler-based plant sensor (103), the stripper plate plant sensor (108), and the plant impact sensor (110).

The plant to be harvested may be planted in a row.

The plant to be harvested may be a corn plant.

DETAILED DESCRIPTION

Figure 1:
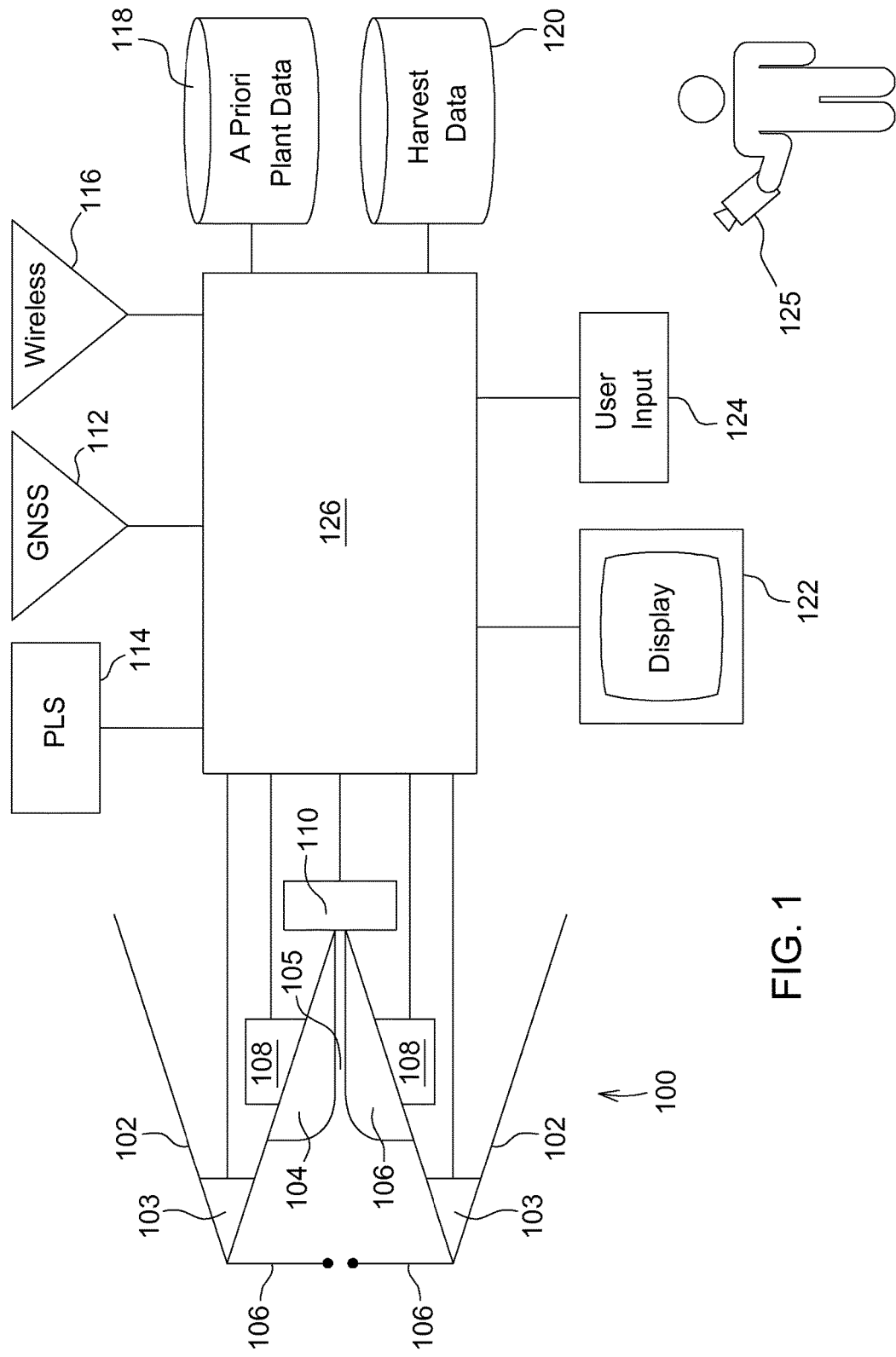
FIG. 1 illustrates a system using plant maps to improve harvest data.

Referring to FIG. 1, a row unit 100 for harvesting corn is disposed between two crop dividers 102. The row unit 100 includes two stripper plates 104 that are spaced apart and define a gap 105 therebetween in which the stalks of corn plants are received as the row unit 100 and the crop dividers 102 are carried through the field on a corn head to harvest the corn plants.

At a forward end of the two crop dividers 102 are vehicle guidance sensors 103. These sensors are used to steer the corn head as it travels through the field. The vehicle guidance sensors 103 include feelers 106 that extend into the gap between the two crop dividers 102. The feelers 106 are disposed to be deflected rearward by the stalks of corn plants.

A first plant attribute sensor 108, (here shown as a stripper plate plant sensor) is coupled to the stripper plates 104 and is configured to generate a signal that indicates the gap between the stripper plates. The gap is normally zero when a corn plant is not present, but when a corn plant is drawn backward between the stripper plates 104 by forward movement of the corn head through the field, the gap between the stripper plates 104 is equal to the thickness (diameter) of the stalk of the corn plant.

A second plant attribute sensor 110, (here shown as a plant impact sensor), is coupled to the stripper plates 104 to generate a signal indicative of the impact of an ear of corn on the stripper plates 104.

A localization circuit 112, such as a GNSS or GPS, provides a signal indicative of a location of the row unit 100 in the field being harvested.

A phytolocation circuit, 114 provides a signal indicative of a location of a plant or plants in the field being harvested.

A radio communication circuit 116 is provided to permit radio communication to a remote ECU. It is configured to transmit data to and from remote locations in a distributed processing arrangement or to transmit harvest data for remote storage, or to provide data on a remote display.

A first digital data storage device 118 is provided to store and retrieve data about plants, such as two-dimensional or three-dimensional locations of individual plants in the field being harvested, the expected yield of these individual plants, the mass of grain of these individual plants. In its initial configuration, the first digital data storage device 118 includes an a priori map of two-dimensional or three-dimensional locations of individual plants in the field being harvested.

A second digital data storage device 120 is provided to store and receive harvest data gathered during the harvesting of the corn plants.

A display device 122 is provided to display data to communicate data to a human such as an operator, site manager, an owner, or other person. The display device may be configured to display per-plant, per-row, or other aggregated plant data or machine guidance information.

A user input device 124 is provided to transmit information from a human such as an operator, a site manager, an owner, or other person.

The display device 122 and the user input device 124 may be local devices carried through the field as crops are harvesting on the same combine harvester that is carrying the corn head on which the row unit 100 is mounted, or they may be remote devices, for example a remote user input device and display device 125.

An electronic control unit (ECU) 126 is coupled to the vehicle guidance sensors 103, the first plant attribute sensor 108, the second plant attribute sensor 110, the localization circuit 112, the phytolocation circuit 114, the radio communication circuit 116, the first digital data storage device 118, the second digital data storage device 120, the display device 122, and the user input device 124.

The ECU 126 comprises a microprocessor and a memory circuit storing digital instructions that control its operation. The ECU 126 may comprise a single processor that is on board the combine harvester that supports the corn head on which the row unit 110 is mounted as it travels through the field harvesting crop. Alternatively, the ECU 126 may comprise a plurality of processors that are on board the combine harvester. Alternatively, the ECU 126 may comprise a network of one or more remote processors that are in communication with one or more onboard processors.

Figure 2:
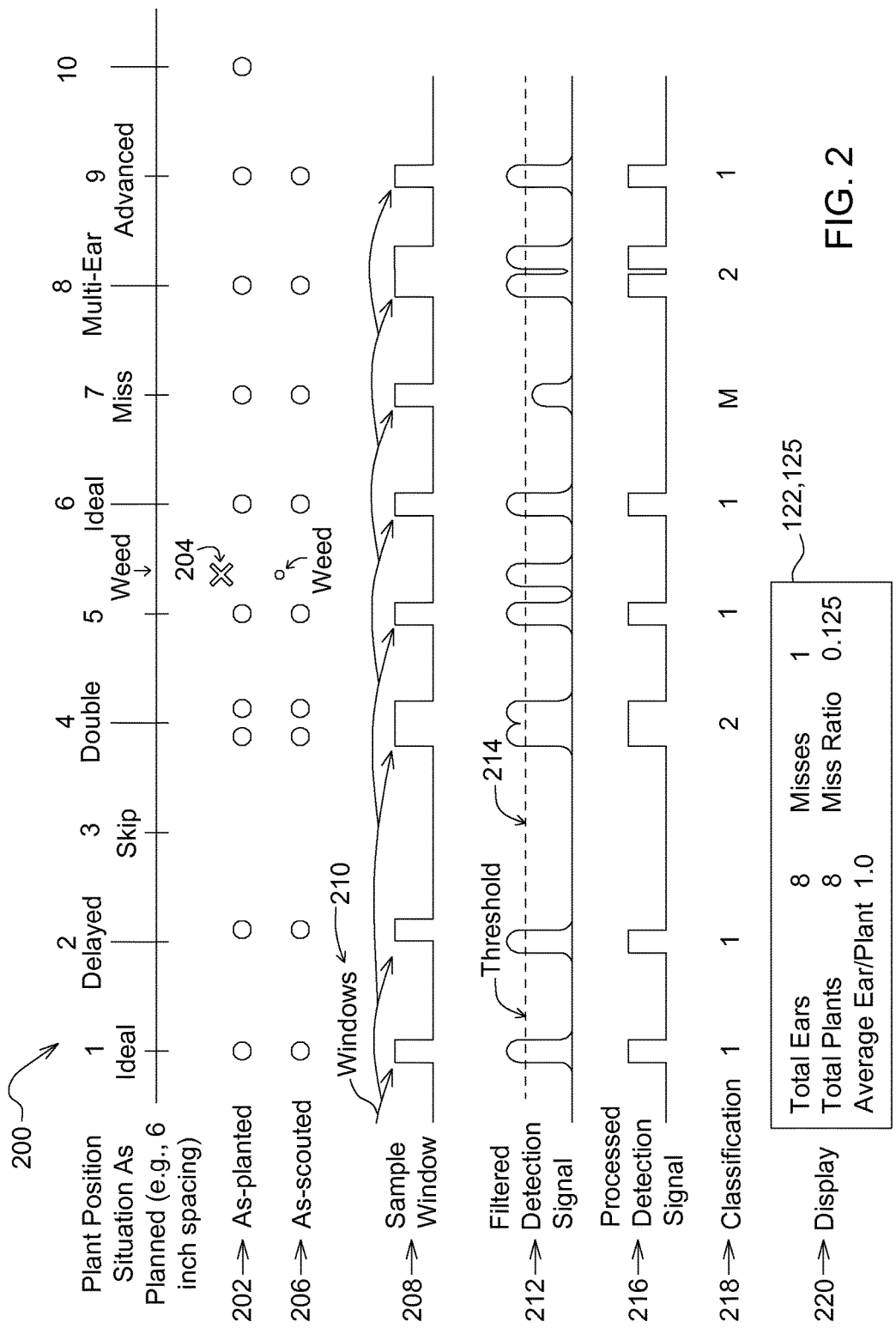
FIG. 2 illustrates an example of how the system of FIG. 1 uses plant maps to filter the signals from plant attribute sensors.

FIG. 2 illustrates the operation of the system for measuring plant attributes using a priori plant maps. In FIG. 2, the various stages of processing and using the plant data by the present invention are shown in example form.

The example shows a segment of one row of corn plants in which 10 plants should have been spaced at regular intervals of 6 inches apart. This regular, ideal spacing of each seed is indicated by the hashmarks on line 200. In line 200, the distance between each plant is the same. In the example of FIG. 2, not all of the seeds have been planted in the preferred locations, nor has every preferred location received a seed. Row 202 shows the several cases:

1. Ideal—the seed was planted in the ideal location
2. Delayed—the seed was slightly delayed in its planting (by accident) and is therefore not quite in its ideal location
3. Skip—no seed was planted at all (by accident).
4. Double—two seeds were planted at a location by accident instead of one seed.
5. Ideal—the seed was planted in the ideal location.
6. Ideal—the seed was planted in the ideal location.
7. Advanced—the seed was planted slightly before its ideal location (by accident).

The row 202 indicates the actual spacing of the seeds, as planted, which in the example of FIG. 2 is six-inch spacing between adjacent seeds.

The row 206 shows the location of each corn plant as that plant has grown. This location data can be gathered by cameras or other sensors during field operations such as spraying the field or fertilizing the field after the seeds have germinated and the corn plants have grown. Alternatively, location data could be collected by a dedicated scout vehicle such as an autonomous terrestrial or aerial robot (i.e. drones). The location of the plants will be the same as the location of the seeds from which they grew. Note that in row 206, the row of location data as-scouted, seed number 10 has failed to germinate and therefore the scout vehicle has not identified any plant corresponding to location 10.

Row 208 shows sensor sample windows 210 for each of the plants identified in the as-scouted a priori plant map. The term "sensor sample window" or "window" as used herein defines a region of time within which ECU 126 is configured to read signals from the first plant attribute sensor 108 and signals from the second plant attribute sensor 110, to process these signals as indicative of plant attributes, and to save these plant attributes to the first digital data storage device 118. Outside of the windows, the ECU 126 is configured to not read signals from sensors 108 and 110. During the windows, data from sensors 103, 108, and 110 will be accepted and processed. During other times, data from sensors 103, 108, 110 will be ignored. Note that weed 204 is ignored because its stem is encountered outside the sample window for either the plant at the location 5 and the plant location 6. This illustrates one way in which noise (in this case the presence of a weed) is rejected by the system.

The ECU is configured to retrieve data from the a priori plant map as the combine harvester travels through the field. The ECU is configured to compare the location of the row unit and its sensors (which is provided to the ECU by the localization circuit) with the locations of each plant the vehicle is approaching (which is provided by the a priori plant map) and to create a window based upon this comparison. Knowing the location of the plants and the location of the row unit, the ECU can begin sampling sensors 103, 108, 110 just as (or slightly before) each plant arrives at the row unit, and stop sampling sensors 103, 108, 110 just after the row unit passes over the plant location and the plant has been processed. This starting point and stopping point of sampling defines the sensor sampling window.

Row 212 shows a filtered plant detection signal originating from one or more of sensors 103, 108, and 110. The filtering removes noise caused by machine vibration, plant leaves, and other extraneous sources. The filtered signal may be proportional and duration or magnitude to the diameter of the plant stalk.

The ECU 126 is configured to identify a plant whenever the filtered detection signal from row 212 exceeds a magnitude threshold 214. The ECU 126 output of this thresholding is depicted in row 216 as a series of pulses of varying width.

The ECU 126 is configured to classify each of the pulses shown in row 216 according to their width. The output of this classification is shown in row 218. In this embodiment, the ECU 126 is configured to generate a count of each ear of corn, and the numerals that comprise row 218 represent the number of ears for each of the plants identified in the a priori plant map.

Finally, the ECU 126 is configured to compile the data it calculated and transmit it to the display device 122, or alternatively the display device 125 as shown in row 220.

The invention is defined by the claims, and not by the examples described above and illustrated in the Figures. The description and figures are provided simply to illustrate one possible arrangement of the invention. Other variations of the invention are contemplated.

The invention claimed is:

1. A system for measuring plant attributes during harvesting of a row crop comprising:
    a harvester having a row unit with stripper plates forming a gap therebetween to receive an individual plant in a row;
    a plant attribute sensor coupled to the row unit;
    a digital a priori plant location map identifying an anticipated presence of the individual plant in the row of plants; and
    an electronic control unit (ECU) coupled to the plant attribute sensor and configured to retrieve and use the a priori plant location map to anticipate presence of the individual plant to be harvested and to use the anticipated presence of the individual plant as part of determining a yield of the individual plant based upon signals the plant attribute sensor.

2. The system of claim 1 wherein the ECU is configured to create a sensor sampling window based upon the anticipated presence of the individual plant as identified in the digital a priori plant location map, wherein the ECU is further configured to receive data from the plant attribute sensor during the sensor sampling window and wherein the ECU is further configured to reject data from the plant attribute sensor outside of the sensor sampling window.

3. The system of claim 2 wherein the plant attribute sensor comprises at least one of a feeler-based plant sensor, a stripper plate plant sensor, and a plant impact sensor.

4. The system of claim 3, wherein the plant attribute sensor comprises the feeler-based plant sensor and wherein the feeler-based plant sensor is a vehicle guidance sensor.

5. The system of claim 3, wherein the plant attribute sensor comprises the stripper plate plant sensor and wherein the stripper plate plant sensor is configured to generate a signal indicative of a plant stalk thickness for a crop plant disposed between two stripper plates.

6. The system of claim 3, wherein the plant attribute sensor comprises the plant impact sensor and wherein the plant impact sensor is configured to respond to impacts of ears of corn on a stripper plate.

7. The system of claim 3, wherein the system further comprises a second plant attribute sensor, wherein the second plant attribute sensor is coupled to the ECU, and wherein the second plant attribute sensor comprises at least another of the feeler-based plant sensor, the stripper plate plant sensor, and the plant impact sensor.

8. The system of claim 1 wherein the anticipated plant presence is used to adjust a value of as-received data from the plant attribute sensor.

9. The system of claim 1, wherein the plant to be harvested is a corn plant.

10. A system for measuring plant attributes during harvesting of a row crop comprising:
    a harvester having a row unit with stripper plates forming a therebetween to receive an individual plant in a row;
    a plant attribute sensor coupled to the row unit; and
    an electronic control unit (ECU) coupled to the plant attribute sensor and configured to: retrieve an a priori plant location map identifying an anticipated presence of the individual plant in the row of plants; receive signals from the plant attribute sensor; and determine plant measurements from (1) signals received from the plant attribute sensor and (2) the anticipated presence of the individual plant as identified by the retrieved a priori plant location map, wherein the ECU is configured to create a sensor sampling window based upon the anticipated presence of a plant based upon the retrieved a priori plant location map, wherein the ECU is further configured to receive data from the plant attribute sensor during the sensor sampling window and wherein the ECU is further configured to reject data from the plant attribute sensor outside of the sensor sampling window.

11. The system of claim 10 wherein the anticipated plant presence is used to adjust a value of as-received data from the plant attribute sensor.

12. The system of claim 10, wherein the plant attribute sensor comprises at least one of a feeler-based plant sensor, a stripper plate plant sensor, and a plant impact sensor.

13. The system of claim 10, wherein the ECU is configured to control sampling starting points and stopping points of the plant attribute sensor based upon the anticipated presence of a plant based upon the retrieved a priori plant location map.

14. The system of claim 10 further comprising the a priori plant location map, wherein the a priori plant location map maps plant location data with respect to plant spacing of a to be harvested plant, the plant location data selected from a group of plant location data consisting of: planned to be harvested plant location; delayed to be harvested plant location; early to be harvested plant location; skipped to be harvested plant location; double to be harvested plant location; weed location; missing to be harvested plant location; and multi-ear to be harvested plant location.

15. The system of claim 10 further comprising the a priori plant location map, wherein the a priori plant location map is based upon planting data.

16. The system of claim 10 further comprising the a priori plant location map, wherein a priori plant location map is based upon to be harvested—plant post emergence preharvest data.

17. A system for measuring plant attributes during harvesting of a row crop comprising:
    a harvester having a row unit with stripper plates forming a gap therebetween to receive an individual plant in a row;
    a plant attribute sensor coupled to the row unit; and
    an electronic control unit (ECU) coupled to the plant attribute sensor and configured to: retrieve an a priori plant location map identifying an anticipated presence of the individual plant in the row of plants; receive signals from the plant attribute sensor; and determine plant measurements from (1) signals received from the plant attribute sensor and (2) the anticipated presence of the individual plant as identified by the retrieved a priori plant location map, wherein the anticipated plant presence is used to adjust a value of as-received data from the plant attribute sensor.

* * * * *